United States Patent [19]

Rajadhyaksha et al.

[11] Patent Number: 5,162,315
[45] Date of Patent: Nov. 10, 1992

[54] PENETRATION ENHANCERS

[76] Inventors: Vithal J. Rajadhyaksha, 5724 Remington Cir., #1709, Fort Worth, Tex. 76132; Richard S. Graham, 5066 Balsawood, Irvine, Calif. 92715

[21] Appl. No.: 348,387

[22] Filed: May 8, 1989

[51] Int. Cl.$^5$ .................................. A01N 31/55
[52] U.S. Cl. .................................... 514/211
[58] Field of Search ........................ 514/211

[56] References Cited

PUBLICATIONS

Chem. Abst. 110-13597q (1989).

*Primary Examiner*—S. J. Friedman
*Attorney, Agent, or Firm*—Grant L. Hubbard

[57] ABSTRACT

Pharmaceutical compositions for enhancing absorption of a topically administered formulation through dermal or mucosal membrane, for local or systemic application, comprising one or more agents of formula I:

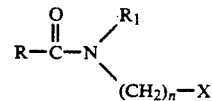

where:

R is a saturated or unsaturated, straight or branched, cyclic or acyclic hydrocarbon group with from 1 to 19 carbon atoms or an alkoxyalkyl group; n is 2-20; X is selected from H, $OR_2$ or $NR_2R_3$; wherein $R_1$, $R_2$ and $R_3$ are independently selected from H, alkyl, haloalkyl, acyl, carbalkoxy, carbalkoxyalkyl, hydroyalkyl, acyloxyalkyl, alkoxyalkyl, aminoalkyl- and acylaminoalkyl; i) with the proviso that when n is 2, X is $OR_2$ and $R_2$ is H, then $R_1$ is not hydroxyalkyl, specifically, 2-hydroxyethyl; and ii) with the proviso that when n is 2 and X is $NR_2R_3$, then $R_1$ and $R_2$ may combine to form a heterocyclic ring and $R_3$ is not acyl; and iii) with the proviso that when X is $NR_2R_3$, then $R_2$ and $R_3$ may combine to form a heterocyclic ring; iv) with the proviso that when R is an alkoxyalkyl group then X may be hydrogen and when X is not hydrogen, and v) with the proviso that when X is H, R is not alkyl and $R_1$ is not H and alkyl then $R_1$ and X may combine to form heterocyclic ring and methods of using the same are disclosed.

4 Claims, No Drawings

PENETRATION ENHANCERS

FIELD OF THE INVENTION

This invention relates to compounds for enhancing penetration of pharmaceutical and agricultural agents.

BACKGROUND OF THE INVENTION

Many dermatological pharmaceutical agents are best applied topically to obtain desirable results. Topical application, in the form of creams, lotions, gels, solutions, etc., largely avoids systemic side effects of the agents and permits high concentrations of the drugs at the site of action.

Some therapeutic drugs may also be administered for systemic use through the skin or other body membranes including intranasal and intravaginal application of humans and other animals, utilizing a transdermal device or formulated in a suppository or aerosol spray. For some years, pharmaceutical researchers have sought an affective means of introducing drugs into the bloodstream by applying them to the unbroken skin. Among other advantages, such administration can provide a comfortable, convenient and safe way of giving many drugs now taken orally or infused into veins or injected intramuscularly.

Using skin as the portal for drug entry offers unique potential because transdermal delivery permits close control over drug absorption. For example, it avoids factors that can cause unpredictable absorption from the gastrointestinal tract including changes in acidity, motility, and food content. It also avoids initial metabolism of the drug by the liver known as the first pass effect. Thus, sustained drug delivery through the skin can achieve a high degree of control over blood concentrations of drugs.

Close control over drug concentration in blood can translate readily into safer and more comfortable treatment. When a drug's adverse effects occur at higher concentrations than its beneficial ones, rate control can maintain the concentration that evoke only, or principally, the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal systems that require application infrequently—in some cases, only once or twice weekly—and reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, those susceptible to a higher first pass liver metabolism, or those requiring frequent dosing in oral or injectable form.

Transdermal therapy permits a much wider use of natural substances such as hormones. Often the survival times of these substances in the body are so short that they would have to be taken many times daily in ordinary dosage forms. Sustained transdermal delivery not only provides a practical way of administering these substances but also potentiates their ability to mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of the drug to the circulation over prolonged periods of time to obtain uniform delivery rate and maintain blood levels of the drug. Commencement and termination of drug therapy is initiated by the application and removal of the dosing devices from the skin. Uncertainties of administration through the gastrointestinal tract and the inconvenience of administration by injection are eliminated. Since a high concentration of the drug never enters the body, problems of pulse entry are overcome and metabolic half-life is not a factor of controlling importance.

The greatest problem in applying physiologically active agents topically or transdermally is that the skin is an effective barrier to penetration. The epidermis of the skin has an exterior layer of dead cells called the stratum corneum which is tightly compacted and oily, and which provides an effective barrier against gaseous, solid or liquid chemical agents, whether used alone or in water or in oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use of treating such conditions as inflammation, acne, psoriasis, herpes labialis, herpes genitalis, eczema, infections caused by fungi, viruses and other microorganisms, or other disorders or conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellents and the like.

Physiologically active agents may be applied to the locally affected parts of the body in the form of a solution, cream, lotion or gel utilizing the vehicle system described herein. These agents may also be delivered for systemic use utilizing the vehicle system in a transdermal patch. Vehicles such as USP cold cream, ethanol and various ointments, oils, solvents and emulsions have been used heretofore to apply physiologically active ingredients locally. Most such vehicles are not effective to carry significant amounts of physiologically active agents into and through the skin. One such vehicle is dimethyl sulfoxide, which is described in U.S. Pat. No. 3,551,554.

My previous inventions disclosed in U.S. Pat. Nos. 3,989,816; 3,991,203; 4,122,170; 4,316,893; 4,415,563; 4,423,040; 4,424,210; 4,444,762 describe a method for enhancing the topical administration of physiologically active agents by combining such an agent with an effective amount of a penetration enhancer and applying the combination topically to humans or animals, in the form of a solution, cream, gel, lotion etc. This prior art discloses N-alkyl substituted cyclic lactams as penetration enhancers.

My related U.S. Pat. No. 4,405,616 describes a method for administering systemically active agents through the skin or other body membranes of humans and animals, utilizing a transdermal device or formulation containing an effective amount of a suitable membrane penetration enhancer selected from the disclosed N-alkyl substituted cyclic lactams.

My related U.S. Pat. Nos. 4,461,638 and 4,762,549 describe a method for enhancing delivery of plant nutrients and plant growth regulators and my U.S. Pat. No. 4,525,199 describes an improved method of pest control by enhancing pesticide permeation.

My related U.S. application, Ser. No. 002,387, filed on Jan. 12, 1987, describes a method for enhancing topical and transdermal administration of physiologically active agents with membrane penetration enhancers selected from heterocyclic compounds containing two heteroatoms.

My related U.S. application, Ser. No. 218,316, filed on Jul. 12, 1988, describes a method for enhancing topical and transdermal administration of physiologically active agents with membrane penetration enhancers selected from oxazolidinone and related heterocyclic penetration enhancing compounds.

Penetration enhancers for enhancing systemic administration of therapeutic agents transdermally disclosed in the art include dodecyl pyrrolidone, dimethyl lauramide, dimethyl sulfoxide and hexamethylene lauramide. These agents may be used prior to or concurrently with the administration of the active agent, see, e.g., U.S. Pat. Nos. 4,031,894; 3,996,934; 3,921,636 and 4,743,588.

SUMMARY OF THE INVENTION

The invention relates to compositions for carrying physiologically active agents through body membranes such as skin, and for retaining these agents in body tissues. It further relates to a method of administering systemically active agents through the skin or other body membranes of humans and animals, utilizing a transdermal device or formulation, containing an effective, non-toxic amount of a membrane penetration enhancer having the structural formula I:

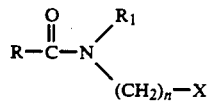

where:

R is selected from saturated or unsaturated, branched or straight acyclic or cyclic hydrocarbon group containing from 1-19 carbon atoms or an alkoxyalkyl group;
n is 2-20;
X is selected from H, $OR_2$ or $NR_2R_3$,
wherein $R_1$, $R_2$ and $R_3$ are independently selected from H, alkyl, haloalkyl, acyl, carboalkoxy, carboalkoxyalkyl, hydroxyalkyl, acyloxyalkyl, alkoxyalkyl, aminoalkyl, alkyl- and acylaminoalkyl; and i) with the proviso that when R is alkyl, n is 2, X is $OR_2$ and $R_2$ is H, then $R_1$ is not H and hydroxyalkyl, specifically, 2-hydroxyethyl; and ii) with the proviso that when n is 2 and X is $NR_2R_3$, then $R_1$ and $R_2$ may combine to form a heterocyclic ring and when R is alkyl then $R_3$ is not acyl; and iii) with the proviso that when X is $NR_2R_3$, $R_2$ and $R_3$ may combine to form a heterocyclic ring;

iv) with the proviso that when R is alkoxyalkyl then X may be hydrogen and when X is not hydrogen $R_1$ and X may combine to form a heterocyclic ring; and v) with the proviso that when X is H, R is not alkyl and $R_1$ is not H and alkyl.

In one preferred embodiment of I,

R is selected from a saturated or unsaturated, branched or straight, acyclic or cyclic hydrocarbon group containing from 5-19 carbon atoms or an alkoxyalkyl group;
n is 2-8;
$R_1$ is H, alkyl or hydroxyalkyl;
X is $NR_2R_3$;
wherein $R_2$ and $R_3$ are independently selected from hydrogen, alkyl, hydroxyalkyl, alkoxyalkyl, aminoalkyl and acylaminoalkyl.

In another preferred embodiment of the composition I, n is 2; X is $NR_2R_3$ wherein $R_2$ and $R_3$ are combined to form an alkylene chain, substituted or unsubstituted, to form a heterocyclic ring structure; and $R_3$ is independently selected from H, alkyl, haloalkyl, carbalkoxy, carbalkoxyalkyl, hydroxyalkyl and alkoxyalkyl; and R is defined as above.

Yet, in another preferred embodiment of I, n is 2-8; X is $NR_2R_3$, where $R_2$ and $R_3$ are combined to form a substituted or unsubstituted heterocyclic ring, for example, pyrrolidine, piperidine, morpholine, piperazine and N-alkylpiperazine; and R and $R_1$ are as defined above.

Yet, in another preferred embodiment of I, R is alkoxyalkyl; X is H; and $R_1$ is as defined above.

Yet, in another preferred embodiment of I, R is alkoxyalkyl; X and $R_1$ are combined to form a heterocyclic ring, for example, pyrrolidine, piperidine, morpholine, piperazine and N-alkylpiperazine.

Yet, in another preferred embodiment of I, X is $OR_2$ and n, R, $R_1$ and $R_2$ are as defined above.

It has been found that the physiologically active agents are carried through body membranes by the claimed penetration enhancers and are retained in the body tissue when applied topically in the form of a cream, gel or lotion or absorbed systemically when applied in the form of a transdermal device or formulation, for example, as a transdermal patch, a rectal or vaginal suppository, as a nasal spray or when incorporated in a vaginal sponge or tampon.

DETAILED DESCRIPTION OF THE INVENTION

Typical examples of compounds included in the foregoing formula I of this invention are the following:

1) N-[2-(2-hydroxyethyl)aminoethyl]dodecanamide
2) N-[2-(2-hydroxyethyl)aminoethyl]-N-ethyl-dodecanamide
3) N-[2-(2-hydroxyethyl)ethylaminoethyl]-dodecanamide
4) N-[2-(2-hydroxyethyl)ethylaminoethyl]-N-ethyl-dodecanamide
5) N-[2-(2-ethoxyethyl)aminoethyl]dodecanamide
6) N-[2-(2-ethoxyethyl)aminoethyl]-N-ethyl-dodecanamide
7) N-[2-(2-ethoxyethyl)ethylaminoethyl]-dodecanamide 8) N-[2-(2-ethoxyethyl)ethylaminoethyl]-N-ethyl-dodecanamide
9) N-[2-(2-hydroxyethyloxy)ethyl]dodecanamide
10) N-[2-(2-hydroxyethyloxy)ethyl]N-ethyl-dodecanamide
11) N-(2-aminoethyl)-N-(2-hydroxyethyl)dodecanamide
12) N-[2-(2-hydroxyethyl)aminoethyl]-N-(2-hydroxyethyl)-dodecanamide
13) N,N-bis-2-(2-ethoxyethyl)dodecanamide
14) N-(2-ethoxyethyl)-N-ethyldodecanamide
15) 1-(1-oxododecyl)-4-(2-hydroxyethyl)piperazine
16) 1-(1-oxododecyl)-4-(2-ethoxyethyl)piperazine
17) 1-(1-oxododecyl)-4-(2-hydroxyethyl)homopiperazine
18) 1-(1-oxododecyl)-4-(2-ethoxyethyl)homopiperazine
19) 1-(1-oxododecyl)-4-ethylpiperazine
20) 1-(1-oxododecyl)-4-ethylhomopiperazine
21) 1-(1-oxododecyl)-4-carbethoxypiperazine
22) 1-(1-oxododecyl)-4-carbethoxymethylpiperazine
23) 1-(1-oxododecyl)-4-(1,1,1,trifluoroethyl)piperazine
24) N-[2-(4-morpholino)ethyl]dodecanamide
25) N-[2-(1-piperidino)ethyl]dodecanamide
26) N,N-diethyl-4-oxa-dodecanamide
27) N-1-oxo-4-oxa-dodecylpiperidine
28) N-1-oxo-4-oxa-dodecylmorpholine The following compounds encompassed by general formula I of this invention are known in the prior art. N-[2-(2-hydroxyethyl)aminoethyl]octadecanamide and N-[2-(2-hydroxyethyl)aminoethyl]pentanamide have been obtained as hydrolysis products from the corresponding imidazolines by Harnsberger and Riebsomer, J. Hetero. Chem. 1, 188 (1964); Gabriel, J. Amer. Oil Chem. Soc., 61, 965 (1984), has described the formation of N-(2-aminoethyl)-N-(2-hydroxyethyl)dodecanamide and N-[2-(2-hydroxyethyl)aminoethyl]dodecanamide as kinetically and thermodynamically controlled products respectively from reaction of N-(2-aminoethyl)aminoethanol and methyl laurate in the presence of catalytic amount of sodium methoxide; Horibatake et al., Jpn. Kokai Tokkyo Koho JP 62,132,946, 16 Jun 1987; C.A. 108, 22881p (1988) claim acylaminoalkyl aminoalkanols, for example, N-[2-(2-hydroxy-ethyl)aminoethyl]dodecanamide, as antistatic agents for synthetic resins; Higuchi and Takahashi, Jpn. Kokai Tokkyo Koho JP 62 57,491, 13 Mar. 1987; C.A. 107, 178711y (1987) claim N-[2-(2-hydroxyethyl) aminoethyl]dodecanamide as being essential in a detergent composition useful for cleaning machines; Moriguchi, Jpn. Kokai Tokkyo Koho JP 62,104,842, 15 May 1987; C.A. 107, 177783m (1987) mentions compositions containing acylaminoalkyleneamines and aminoalcohols as antitack agents for unvulcanized rubbers; Higuchi and Takahashi, Jpn. Kokai Tokkyo Koho JP 61,114,726, 02 Jun 1986; C.A. 105, 155513e (1986) mention the use of N-[2-(2-hydroxyethyl) aminoethyl]dodecanamide and octadec-9-enamide and N-(2-aminoethyl)-N-(2-hydroxyethyl)dodecanamide as emulsifying agents for stable emulsions; Moriguchi, Jpn. Kokai Tokyo Koho JP 71 09,939, 13 Mar 1971; C.A. 76, 60500s (1972) describe the use of N-[2-(2-Hydroxyethyl)aminoethyl]dodecanamide and octadecanamide as heat and water resistant antistatic agents; N-2-aminoethylamides of lower carboxylic acids have been reported by Rosenmund, U.S. Pat. No. 1,926,015 (Sep. 5, 1933); dodecanoic and tetradecanoic acid derivatives (m.p. 51°-2° C. and 62° C.) have been synthesized by Weiner, U.S. Pat. No. 2,387,201 (Oct. 16, 1945) and the latter (m.p. 150°-152° C.) by Kyrides, U.S. Pat. No. 2,399,601 (Apr. 30, 1946), but purity of these compounds is questionable based on the discrepancy in the reported melting points; Harnsberger and Riebsomer have isolated N-[2-(2-hydroxyethyl)aminoethyl]octadecanamide and pentanamide as hydrolysis products from the corresponding imidazolines.

To my knowledge the other compounds are novel.

The use of the compounds of the present invention as penetration enhancers is, however, novel and not predictable from the prior art.

The compounds of the present invention may be used as penetration enhancers in the same manner as described in my U.S. Pat. Nos. 3,989,816; 3,991,203; 4,415,563; 4,122,170; 4,316,893; 4,423,040; 4,424,210; 4,444,762; 4,461,638; 4,525,199 and 4,762,549, and pending U.S. applications Ser. No. 783,621 filed Sep. 30, 1985, Ser. No. 002,387 filed Jan. 12, 1987 and Ser. No. 218,316, filed on Jul. 12, 1988, which are hereby incorporated by reference.

The compounds of the present inventions are useful as penetration enhancers for a wide range of physiologically active agents and the compositions disclosed herein are useful for topical and transdermal therapeutic effect of these agents. Typically, systemically active agents which may be delivered transdermally are therapeutic agents which are sufficiently potent such that they can be delivered through the skin or other membranes to the bloodstream in sufficient quantities to produce the desired therapeutic effect. In general, this includes agents in all of the major therapeutic areas including, but not limited to, anti-infectives, such as antibiotics and antiviral agents, analgesics, anorexics, anthelmintics, antiarthritics, antiasthma agents, anticonvulsants, antidepressants, antidiabetic agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, sedatives and tranquilizers and anti-osteoporosis agents.

For topical applications the agents include antibiotics, fungistatic and fungicidal agents, corticosteroids, antihemorrhoidal agents, antiinflammatory agents, antineoplastic agents, antiemetics, antipruritic agents, vasodilators, bronchodilators, expectorants, analgesics, sunscreen compounds, collagen softening agents and other similar compounds. Cosmetic agents, hair and skin dyes, natural and synthetic hormones, perfumes, insect repellents, diagnostic agents and other such compounds may also be advantageously formulated with these penetration enhancers.

Moreover, these penetration enhancers are useful in agriculture in the application of fertilizers, hormones, growth factors including micronutrients, insecticides, molluscicides, arichicides, nematocides, rodenticides, herbicides, and other pesticides to plants, animals and pests. These penetration enhancers are also useful for penetration of micronutrients in seeds for enhanced plant growth.

Of course, the appropriate dosage levels of all the physiologically active agents, without conjoint use of the penetration enhancing compounds of formula I, are known to those of ordinary skill in the art. These conventional dosage levels correspond to the upper range of dosage levels for compositions including a physiologically active agent and a compound of formula I as a penetration enhancer. However, because the delivery of the active agent is enhanced by compounds of the present invention, dosage levels significantly lower than conventional dosage levels may be used with success. Systemically active agents are used in amounts calculated to achieve and maintain therapeutic blood levels in a human or animal over the period of time desired. (The term "animal" as used here encompasses humans as well as other animals, including particularly pets and other domestic animals.) These amounts vary with the potency of each systemically active substance, the amount required for the desired therapeutic or other effect, the rate of elimination or breakdown of the substance by the body once it has entered the bloodstream and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The present invention contemplates compositions of compounds of formula I, together with physiologically active agents from 0.05% to 100% of conventional dosage levels. The amount of carboxylic acid amide derivative of formula I which may be used in the present invention is an effective, non-toxic amount for enhancing percutaneous absorption. Generally, for topical use the amount ranges between 0.01 to about 10 and preferably about 0.1 to 5 percent by weight of the composition. For transdermal enhancement of systemic agents, the amount of penetration enhancer which may be used in the invention varies from about 1 to 100 percent, although adequate enhancement of penetration is generally found to occur in the range of about 1 to about 30 percent by weight of the formulation to be delivered. For transdermal use, the penetration enhancers disclosed herein may be used in combination with the active agent or may be used separately as a pretreatment of the skin or other body membranes through which the active agent is intended to be delivered.

Dosage forms for application to the skin or other membranes of humans and animals include creams, lotions, gels, ointments, suppositories, sprays, aerosols, buccal and sublingual tablets and any one of a variety of transdermal devices for use in the continuous administration of systemically active drugs by absorption through the skin, oral mucosa or other membranes, see for example, one or more of U.S. Pat. Nos. 3,598,122; 3,598,123; 3,731,683; 3,742,951; 3,814,097; 3,921,636; 3,972,995; 3,993,072; 3,993,073; 3,996,934; 4,031,894; 3,972,995; 3,993,072; 3,993,073; 3,996,934; 4,031,894; 4,060,084; 4,069,307; 4,201,211; 4,230,105; 4,292,299 and 4,292,303. U.S. Pat. No. 4,077,407 and the foregoing patents also disclose a variety of specific systemically active agents which may also be useful as in transdermal delivery, which disclosures are hereby incorporated herein by this reference.

Typical inert carriers which may be included in the foregoing dosage forms include conventional formulating materials, such as, for example, water, ethanol, 2-propanol, 1,2-propanediol, 1,3-butanediol, 1,2,3-propanetriol, propanone, butanone, carboxylic acid esters such as isopropyl myristate, diisopropyl adipate and diisopropyl sebacate, acyclic and cyclic amides including N-methyl pyrrolidone, urea, freons, polyvinyl pyrrolidone, fragrances, gel producing materials such as "Carbopol", stearyl alcohol, stearic acid, spermaceti, sorbitan monooleate, sorbital, "Polysorbates", "Tweens", methyl cellulose, etc.

It will be readily appreciated by those skilled in the art that certain compounds represented by general formula I exhibit chirality. However, where no designation of isomers is specified with respect to the compounds of this invention, it is to be understood that all possible stereoisomers are included.

It will also be readily appreciated by those skilled in the art that certain compounds represented by general formula I may form salts with carboxylic and mineral acids and it is to be understood that all such salts are included in this invention.

The examples which follow illustrate the penetration enhancers and the compositions of the present invention. However, it is understood that the examples are intended only as illustrative and are not to be construed as in any way limiting to the scope of this invention.

EXAMPLE 1

Preparation of
N-[2-(2-hydroxyethyl)aminoethyl]dodecanamide 22 g of 1-(2-hydroxyethyl)-2-undecyl-2-imidazoline and 300 ml of water was stirred at 40°-50° C. for 24 hours. The resulting soapy solution was salted with 50 g of NaCl and then extracted with 500 ml ethyl acetate. The organic layer was dried, filtered and concentrated to give 23 g of solid. This material was dissolved in hexane by heating at 50 C. for 2 hrs., then cooled to room temperature and filtered to afford 18.8 g of pure product, m.p. 92°-94° C.

EXAMPLE 2

The following compounds were prepared from the appropriately 2-substituted 1-(2-hydroxyethyl)-2-imidazoline according to the procedure of Example 1.
N-[2-(2-hydroxyethyl)aminoethyl]octanamide, m.p. 75°-77° C., N-[2-(2-hydroxyethyl)aminoethyl]octadec-9-enamide, waxy solid.

EXAMPLE 3

Preparation of
N-[2-(2-hydroxyethyloxy)ethyl]dodecanamide

To a cooled solution of 11 g of 2-(2-aminoethoxy)-ethanol in 75 ml of dichloromethane and excess triethylamine was added dropwise 13 g of dodecanoyl chloride in 25 ml of dichloromethane. After stirring at room temperature for 3 hours the reaction mixture was concentrated and then diluted with 100 ml of ethyl acetate and 100 ml of water. The organic layer was washed with 2×50 ml of water and brine, dried, filtered and concentrated to give 13.7 g of crude product. Recrystallization from ethyl acetate/hexane gave 11.2 g of product, m.p. 62°-64° C.

EXAMPLE 4

Preparation of N-[2-(2-hydroxyethyl)aminoethyl]-N-(2-hydroxyethyl)dodecanamide 5.3 g of N,N'-Bis(2-hydroxyethyl)ethylenediamine and 3.0 g of dodecanoyl chloride were reacted together following the procedure under Example 3. This provided 3.3 g of pure product, m.p. 94° C.

EXAMPLE 5

Preparation of 1-(1-oxododecyl)-4-(2-hydroxyethyl)piperazine 5.2 g of 1-(2-hydroxyethyl)piperazine and 8.8 g of dodecanoyl chloride was reacted following the procedure under Example 3. This provided 8.7 g of product, m.p. 38°–40° C.

EXAMPLE 6

Preparation of N-(2-aminoethyl)dodecanamide

A solution of 23 g of ethyl dodecanoate and 62.7 g of ethylenediamine in 100 ml of tetrahydrofuran (THF) was refluxed for 3 hours and the excess THF was distilled off. The reaction mixture was heated at 100° C. for 16 hours, cooled to room temperature, poured into cold water and extracted with ether. After drying, the organic solution was concentrated to give 15.7 g of crude product and this was recrystallized from ether-hexane to give 10.9 g of pure product, m.p. 64°–66° C.

EXAMPLE 7

Preparation of N-[3-(4-morpholino)propyl]dodecanamide 22.0 g of 4-(3-aminopropyl)morpholine and 14.5 g of dodecanoyl chloride was reacted following the procedure under Example 3. This provided 29.3 g of product, m.p. 50°–52° C.

The compounds of the present invention were tested in vitro as penetration enhancers according to the procedure outlined below. The penetration enhancers were formulated with pharmacologically active agents in creams and permeation of the active agent through human stratum corneum in vitro was compared to control formulation without enhancer. Higher permeation of the active agent in presence of an enhancer exemplified the invention.

EXAMPLE 8

Human stratum corneum was isolated from full thickness human skin as described by Bronaugh et al., J. Pharm. Sci. 75, 1094 (1986). The skin was placed between the donor and the receptor compartments of diffusion cells in such a way that the dermal side of the skin faced the receptor compartment which was filled with normal saline (pH 7.2–7.4). The stratum corneum was equilibrated at 37° C. overnight prior to the application of a topical formulation or transdermal patch. All formulations were studied in triplicate.

About 500 mg of the following three Isosorbide Dinitrate (ISDN) formulations (40% ISDN & 60% Lactose) were applied to cover the stratum corneum surface within the donor compartment. The entire contents of the receptor compartment were removed at specific time intervals over 48 hours and replenished with fresh saline. The aliquots were analyzed by HPLC and the average cumulative amount of ISDN in micrograms permeating over the study period was calculated.

| Cream Formulation | Average Cumulative Amount of ISDN in Micrograms permeating over 48 hours |
|---|---|
| 1) 0.7% ISDN (Control) | 535.0 ± 25 |
| 2) 0.7% ISDN + 2% 1-(2-hydroxyethyl)-2-undecyl-2-imidazoline | 872.3 ± 85 |
| 3) 0.7% ISDN + 2% Enhancer of Example 1 | 821.3 ± 56 |
| 4) 0.7% ISDN + 2% Enhancer of Example 5 | 1160.9 ± 73 |

The results clearly showed that Enhancers of Examples 1 and 5 had superior permeation enhancing properties as compared to control and Enhancer of Example 1 was as effective as its cyclic isomer.

EXAMPLE 9

Procedure of Example 8 was repeated with the following

| Hydrocortisone (HC) cream formulations. | |
|---|---|
| Cream Formulation | Average Cumulative Amount of HC in Micrograms permeating over 48 hours |
| 1) 0.5% HC (Control) | 27.72 ± 1.84 |
| 2) 0.5% HC + 2% 1-(2-hydroxyethyl)-2-undecyl-2-imidazoline | 67.53 ± 3.34 |
| 3) 0.5% HC + Enhancer of Example 1 | 55.19 ± 5.16 |

The results clearly showed that the formulation containing Enhancer of Example 1 showed superior permeation as compared to control cream and was as effective as its cyclic isomer.

EXAMPLE 10

Procedure of Example 8 was repeated with the following Haloperiodol Decanoate (HD) cream formulations. Saline in the receptor compartment was substituted with saline/isopropyl alcohol (1:1).

| Cream Formulation | Average Cumulative Amount of HD in Micrograms permeating over 51 hours |
|---|---|
| 1) 5% HD (Control) | 617.68 ± 17.68 |
| 2) 5% HD + 3% Enhancer of Example 5 | 936.66 ± 16.98 |

The results clearly show that the formulation containing Enhancer of Example 5 showed higher HD permeation as compared to control.

EXAMPLE 11

Example 8 is repeated, except the Isosorbide Dinitrate is substituted by 0.5–10% amount by weight of each of the following therapeutically active agents.

| % | |
|---|---|
| 1–10 | Indomethacin |
| 1–10 | Diclofenac |
| 1–10 | Propranolol |
| 0.5–5 | Fentanyl |
| 0.5–5 | Naloxone |

| % | -continued |
|---|---|
| 0.5-5 | Hydromorphone |
| 1-10 | Diltiazem |
| 1-10 | Nicardipine |
| 1-10 | Albuterol |
| 1-10 | Metaproterenol |
| 0.1-3 | Clonidine |
| 0.1-3 | 5-Fluorouracil |
| 0.5-5 | Acyclovir |
| 0.1-3 | Triazolam |
| 0.5-5 | Lisinopril |
| 0.5-5 | Clindamycin |
| 1-10 | Miconazole |
| 1-10 | Griseofulvin |

While particular embodiments of the invention have been described it will be understood of course that the invention is not limited thereto since many obvious modifications can be made and it is intended to include within this invention any such modifications as will fall within the scope of appended claims.

INDUSTRIAL APPLICATION

This invention is useful in the pharmaceutical and agricultural industries and in the preparation of compositions for cosmetic, diagnostic and therapeutic use.

What is claimed is:

1. A pharmaceutical composition for enhancing absorption of a topically administered formulation through dermal or mucosal membrane, for local or systemic application, comprising a therapeutically effective amount of the pharmaceutically active cardiovascular agent diltiazem and a non-toxic, effective amount of a membrane penetration enhancing agent of formula:

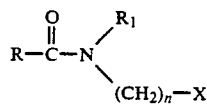

where
R is a saturated or unsaturated, straight or branched, cyclic or acyclic hydrocarbon group with from 1 to 19 carbon atoms or an alkoxyalkyl group;
n is 2-20;
X is selected from H, $OR_2$ or $NR_2R_3$;
wherein $R_1$, $R_2$ and $R_3$ are independently selected from H, alkyl, haloalkyl, acyl, carbalkoxy, carbalkoxyalkyl, hydroxyalkyl, acyloxyalkyl, alkocyalkyl, aminoalkyl, alkyl- and acylaminoalkyl;
i) with the proviso that when n is 2, X is $OR_2$ and $R_2$ is H, then $R_1$ is not hydroxyalkyl; and
ii) with the proviso that when n is 2 and X is $NR_2R_3$, then $R_1$ and $R_2$ may combine to form a heterocyclic ring and $R_3$ is not acyl; and
iii) with the proviso that when X is $NR_2R_3$, then $R_2$ and $R_3$ may combine to form a heterocyclic ring;
iv) with the proviso that when R is an alkoxyalkyl group then X may be hydrogen and when X is not hydrogen, then $R_1$ and X may combine to form a heterocyclic ring; and
v) with the proviso that when X is H, R is not alkyl and $R_1$ is not H or alkyl.

2. A method for enhancing the rate of dermal or mucosal membrane absorption of a topically administered composition for local or systemic application, comprising a therapeutically effective dosage amount of the pharmaceutically active cardiovascular agent diltiazem and a non-toxic, effective amount of a membrane penetration enhancing agent of formula:

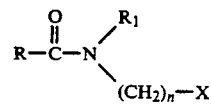

where
R is a saturated or unsaturated, straight or branched, cyclic or acyclic hydrocarbon group with from 1 to 19 carbon atoms or an alkoxyalkyl group;
n is 2-20;
X is selected from H, $OR_2$ or $NR_2R_3$;
wherein $R_1$, $R_2$ and $R_3$ are independently selected from H, alkyl, haloalkyl, acyl, carbalkoxy, carbalkoxyalkyl, hydroxyalkyl, acyloxyalkyl, alkoxyalkyl, aminoalkyl, alkyl- and acylaminoalkyl;
i) with the proviso that when n is 2, X is $OR_2$ and $R_2$ is H, then $R_1$ is not hydroxyalkyl; and
ii) with the proviso that when n is 2 and X is $NR_2R_3$, then $R_1$ and $R_2$ may combine to form a heterocyclic ring and $R_3$ is not acyl; and
iii) with the proviso that when X is $NR_2R_3$, then $R_2$ and $R_3$ may combine to form a heterocyclic ring; and
iv) with the proviso that when R is an alkoxyalkyl group then X may be hydrogen and when X is not hydrogen, then $R_1$ and X may combine to form a heterocyclic ring; and
v) with the proviso that when X is H, R is not alkyl and $R_1$ is not H or alkyl.

3. The method of claim 2 wherein said agent is 1-(1-oxododecyl)-4-(2-hydroxyethyl)piperazine.

4. A pharmaceutical composition comprising a therapeutically effective amount of diltiazem and a non-toxic, effective amount of 1-(1-oxododecyl)-4-(2-hydroxyethyl)piperazine as a membrane penetration enhancing agent.

* * * * *